United States Patent [19]

Rock

[11] 4,128,476

[45] Dec. 5, 1978

[54] CARRIER COMPOSITION CONTROL FOR LIQUID CHROMATOGRAPHIC SYSTEMS

[75] Inventor: John V. Rock, Los Altos, Calif.

[73] Assignee: Spectra-Physics, Inc., Mountain View, Calif.

[21] Appl. No.: 806,456

[22] Filed: Jun. 14, 1977

[51] Int. Cl.² .......................................... B01D 15/08
[52] U.S. Cl. .................................. 210/31 C; 210/101; 210/137; 210/138; 210/198 C
[58] Field of Search ..................... 210/31 C, 101, 137, 210/138, 139, 198 C

[56] References Cited

U.S. PATENT DOCUMENTS

| | | | |
|---|---|---|---|
| 3,917,531 | 11/1975 | Magnussen | 210/101 |
| 4,032,445 | 6/1977 | Munk | 210/198 C |
| 4,043,906 | 8/1977 | Helmer | 210/31 C |
| 4,045,343 | 8/1977 | Achener et al. | 210/101 |

Primary Examiner—John Adee

[57] ABSTRACT

In the cycle of a positive displacement LC pump system the output pressure is sensed to measure onset of output flow as a time lag from the beginning of the output stroke to give an estimate of the input filling time lag from the beginning of the fill stroke. This estimate is used to recompute a proportional module output for controlling the timing of a proportioning valve at the inlet to the LC pump so as to bring the actual operating conditions of the pump fill cycle into correspondence with the predetermined demanded ratios of the components either in isocratic or gradient program mode.

3 Claims, 5 Drawing Figures

CARRIER COMPOSITION CONTROL FOR LIQUID CHROMATOGRAPHIC SYSTEMS

BACKGROUND OF THE INVENTION

This invention relates to liquid chromatographic systems and more particularly to systems as used in either isocratic or gradient elution of a liquid carrier serving as a mobile phase together with a sample transported thereby through a stationary phase. Generally, the stationary phase is mounted as a packed or open tubular column within an elongate container one end of which is provided with a sample injector and is connected at that end to the output of a pump for delivering the carrier under high pressure. In current systems, the carrier is delivered at pressures which may be as high as in the range of 3,000 to 7,000 psi and even greater.

The carrier phase in isocratic work comprises a fixed proportion of components, for example, 50% water and 50% methanol, while the carrier phase in gradient elution work is programmed to vary between desired values of proportions, i.e., from 90% water–10% methanol, up to 10% water and 90% methanol, over a predetermined interval of time. The central problem of the methods and apparatus for high pressure liquid chromatography (HPLC) work from the point of view of the analytical chemist requires that the system supply a constant flow rate through the column of a known isocratic composition or proportion or known gradient elution composition according to predetermined settings.

It is a primary object of the present invention to provide a liquid chromatographic system which is reliable in both isocratic or gradient proportion operation to provide a known, predetermined composition of the various components of the carrier in accordance with the preset demand.

The problem which must be overcome includes, for example, the actual compressibility of carrier liquid components, the nonlinear variation of their compressibility as a function of liquid component mixtures, the compressibility of pump components including seals, walls, pistons, valves and the like. Reference is made to an article by Klaus Keck, entitled "A New Gradient Mixer for Column Chromatography", *Analytical Biochemistry*, 39, pages 288 to 296 (1971), showing a typical system for time share mixing of isocratic and gradient carrier mixtures of liquids using switched solenoid valves which are programmed in accordance with various on-off states by a program card and therein showing the mixing occured at atmospheric pressure. In Keck, the mixed solution thereafter is applied to a mixing tank before being drawn off by a suitable pump for insertion into the column. The details of reciprocating pumps and associated components, however, when operated at high pressures causes variations in the amount of each liquid drawn depending upon its location within the fill cycle or stroke. In a typical low pressure solvent mixing system, a reciprocating piston pump is fitted with inlet and outlet check valves, the inlet valve being directed to a take-up carrier source from a storage facility for the same and a programmed valving means which operates at atmospheric pressure through the inlet check valve. On the pump stroke, the pump delivers a charge of the mixture taken up at the indicated high pressure through the output check valve to the column. Thus, if filling with a multi-component mixture A, B, and C, wherein A is taken first, after which the valve switches to B and C, the fill stroke begins by decompression of all the parts as well as the residual or dead volume of the entire pump and associated components, from the high pump stroke pressure to atmospheric fill pressure. By judicious, careful and expensive construction, this decompression volume and the effect thereof can be minimized. However, it is necessary, in any event, to provide piston end clearance, piston and seal tolerances and check valve and connector particulars, all of which contribute to residual volume, as well as the literal dimensional expansion of the pump cylinder walls and compression seals and the like, all of which contribute unknown variables in the time lag between the start of the fill stroke at the beginning of decompression and the actual opening of the inlet check valve to take in the first of the components of the carrier. While it might be thought possible to measure inlet check valve opening in some direct way, this has not proved to be practical and the present invention relies on an indirect measurement of inlet check valve opening, which indirect measurement accounts for and provides for compensation for all of the foregoing decompression and residual volume compressibility variables including the compressibility of the carrier·solvent mixture.

SUMMARY OF THE INVENTION AND OBJECTS

Basically, the present invention is predicated upon the realization that the decompression lag caused by pump and associated parts and residual carrier volume before inlet valve opening can be related in a unique way to the compression lag upon the beginning of the pump stroke. During compression, the pump must operate to bring the working and residual volumes up to operating pressure before the outlet valve will open. At significant operating pressures, an outlet pressure transducer will notice a slight pressure drop in the input to the LC column at the beginning of one pump stroke and just prior to outlet valve opening. The maximum excursion or dip occurs just prior to the opening of the outlet valve at the beginning of the pumping stroke. The timing of the dip maximum is found to vary in relation to the reference timing of the pump driving mechanism. This variation is a function of the operating pressure of the pump, the composition of the carrier components as well as all of the factors which contribute to compressibility. More rigorously, it is found that the time for opening of the input valve is related in fixed proportion to the time lag of opening of the outlet check valve on the compression stroke (and that this fixed constant is independent of the solvent used). By measuring this output time lag emperically, the total inlet proportioning valve timing is then recomputed in accordance with the present invention to provide compensated demand values resulting in the desired component ratios of the carrier. With the present invention, this calibration of the carrier composition is carried out in a single initial step and subsequent errors occuring during gradient elution, for example, are accepted as a second order effect. However, it is obvious that the process and system disclosed herein may be operated repetitively at appropriate intervals during a run to recalibrate the system should the same be found necessary.

In practice, this invention utilizes a single dual chamber reciprocating positive displacement pump having opposed pistons driven off a single cam. This cam is shaped to provide a short fill stroke of about 100° and a longer pump stroke of about 180°. The inlet to the pump is connected to parallel inlet check valves to a time proportioning mixing valve connected to suitable individual sources of carrier components to be selected (at minimum or low working pressure). The pump strokes of each opposed chamber are coupled through a parallel connected outlet valve to deliver a constant output flow to the inlet of the column. A pressure transducer measures head at the inlet to the column. A reference signal is generated by the pump cam to suitable means at the beginning of each fill stroke and the time intervals between the occurence of the reference signal and the maximum pressure dip is measured. This time is converted to degrees and ratioed against the desired demand to give a percentage of actual fill cycle used for take-up of that component. A composition computer re-computes the cycle times of the remaining components to give a desired proportion so that at the end of the fill stroke, the proportioning valves will have operated through compensated cycle times and the actual composition delivered to the pump will be that as originally demanded. These and other objects and features of the invention will become apparent from the following description and claims when taken with the accompanying drawings.

BRIEF DESCRIPTION OF THE DRAWINGS

Referring now to FIG. 1, a typical elution chromatograph constructed and modified in accordance with the present invention is shown in schematic form and consists generally of a solvent storage module 10 which contains solvents A, B, and C is respective storage jars 11, 12, 13 connected therefrom by suitable piping 14 to a composition control module 16. The latter consists of three digital valves 18 suitably arranged and controlled in on and off cycle times by a valve sequence driver 20. The output of the valves proceeds through a common line 22 to the input of a pumping module 24 which consists in the usual case of a single dual chamber pump 26, a cam 27 having opposed pistons 28, 30 working in closed end chambers 32, 34, the inlets to which are connected through parallel inlet check valves 36, 38 to the output pipe 22 of the composition control module 16. The output of the pump is connected through suitable parallel connected check valves 40, 42 to the input to a sample injection module through single line 44 incorporating a suitable pressure measuring transducer 46 which may either be of the inline or crossline type. The check valves open and close in response to the crossing of the threshold of pressure equalization across them. After sample injection at module 50, the liquid and carrier mobile phase and sample are continuously flowed into the LC column and separation module 52 after which separation detection is possible by typical means such as ultraviolet visible detecting module shown schematically at 53.

The pump is driven from the single cam 27 in reciprocating fashion in such a way that the cam provides a fill stroke of approximately 100° in which it is backing with respect to a given piston and a subsequent pump stroke of about 180° in which it is pushing the system into its respective chamber. Suitable means are provided for sensing the mechanical beginning of each fill stroke (also the actual beginning at zero working pressure) and may, for example, consist of passages or reflectors 54 or other device associated with the cam for interrupting or passing a light pulse to an LED. This provides a start time measurement for the beginning of each fill cycle of each portion of the pump stroke that at zero working pressure would actually begin the filling of the pump. However, under actual working pressures, the pump will not fill nor the inlet valve open until decompressibility has occured as to all the pump operating parts and the residual volume contained in the pump.

Figure 1:
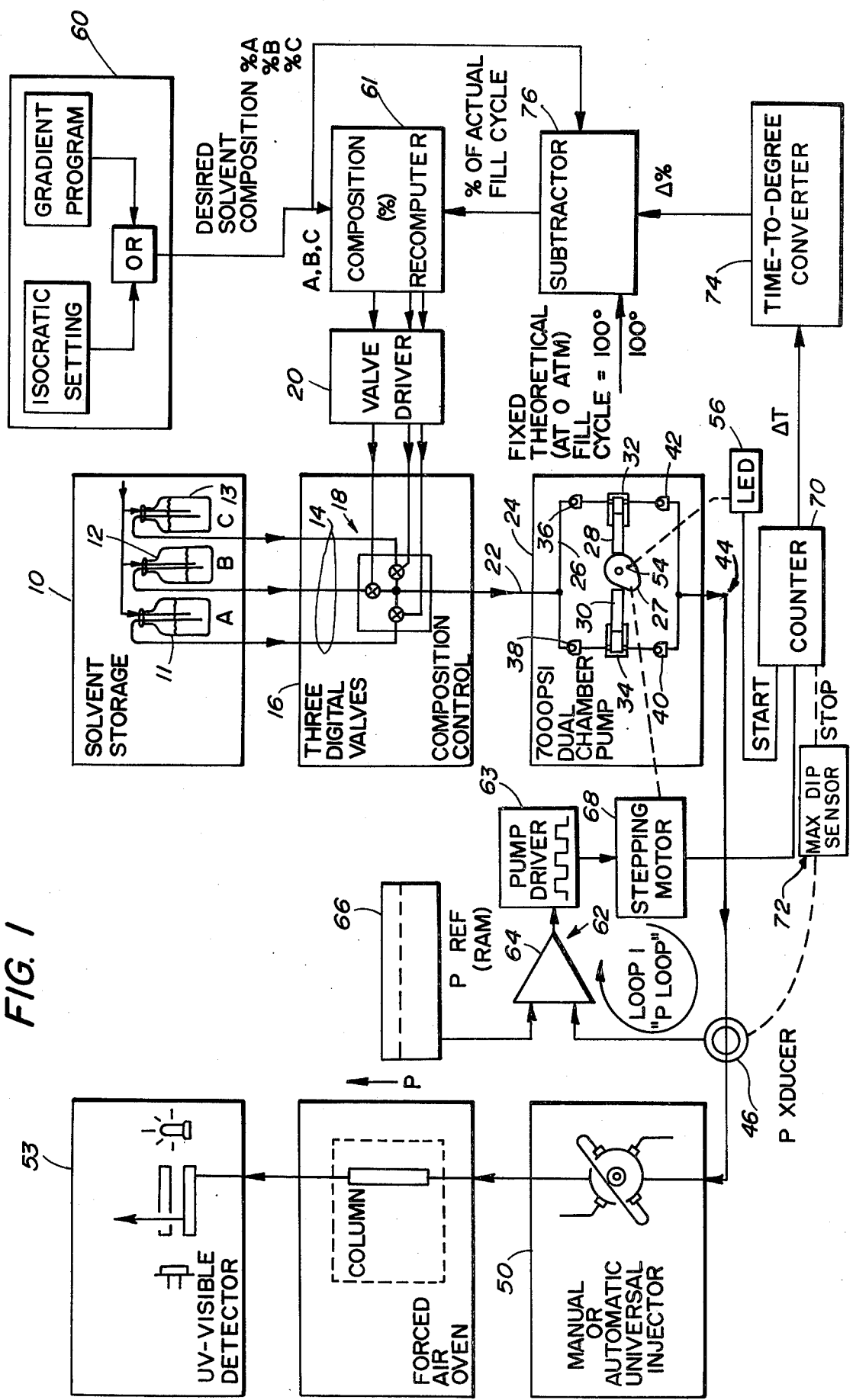
FIG. 1 is a block diagram of a system for carrier or mobile phase composition control of the proportions of a carrier mixture for use in high pressure liquid chromatographs constructed in accordance with the present invention.
Figure 2:
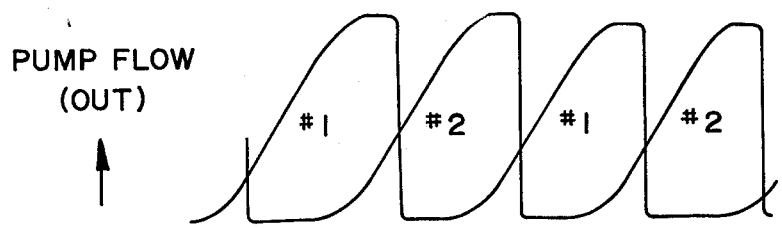
FIG. 2 is a graph showing pump stroke operation for the system of FIG. 1.
Figure 3A:
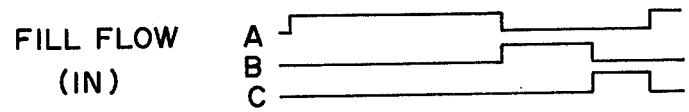
FIG. 3A is a preliminary or initial demand timing diagram for the proportions of component solvents A, B and C with which it is desired to fill the pump of the apparatus of FIG. 1.

A composition control module 60 is provided and is either initiated by an isocratic setting mode which provides a fixed demand proportion between the various components or a gradient program mode which permits variation of the ratio of the components to be made during operation of the chromatograph. The initial solvent component demand outputs are selectively sent through a suitable OR circuit to a composition recomputer module 61. Under usual conditions, a carrier composition delivered to the composition recomputer consists of a demand percentage of A, demand percentage of B and a demand percentage of C, although the latter is obviously computable from the former all of which can be immediately related to the cam angle and speed. The recomputer module controls the actual composition demand as delivered to a valve driver module by controlling the timing of the opening and closing of the digital valves in the composition control module. The composition recomputer is also controlled by the output of a subtractor module which computes a percentage of actual fill cycle accomplished at a given working pressure by the procedures and mechanisms now to be described. If an actual fill cycle, for example, only capable of delivering 94% of the demanded value of the percentage of the component A, the composition recomputer will apply at that percentage to the remaining solvent demand angles or times so as to adjust the operation timing of the valve driver accordingly. The output of the composition control unit is indicated in FIG. 3A while the pump output operation is indicated in FIG. 2. Thus, during the first cycle the pump stroke delivers power up to a predetermined level at which it tapers off and the second stroke begins to take over the load. As is known, the shape of the cam can be constructed to deliver a sum of output flow at zero working pressure which is substantially constant and shown in FIG. 4A.

Figure 3B:
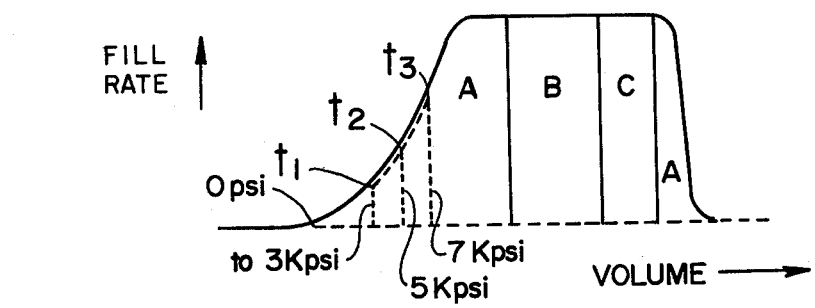
FIG. 3B is an expanded graph of the actual pump stroke fill cycle illustrating details thereof.
Figure 4:
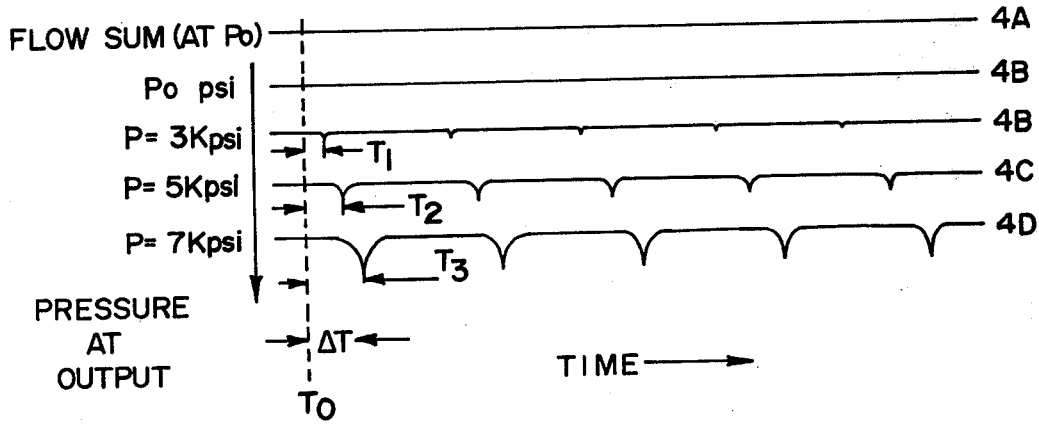
FIGS. 4A, B, C, and D are graphs illustrating output pressure measurements for various operating pressures of the pump apparatus of FIG. 1.

FIG. 3B illustrates the way in which the input stroke volume varies as a function of output working pressure. Thus, at zero working pressure, the pump begins its fill stroke immediately. Whereas, at 3,000 psi, the time has shifted to a time lag position $t_1$. This time continues to shift to ever larger time lag values $t_2$ and $t_3$ at 5,000 and 7,000 psi, respectively. As will be noted, the result includes an error in the amount of the composition of A which is delivered to the pump. Since the pump decompression occurs only during the beginning of the cycle, the direct error for components B and C will not exist but these components, accordingly, must be adjusted for the error in the A composition fill in order that the desired output composition be obtained. FIGS. 4A, B, C, D illustrates the output pump pressure as a function of various operating pressures. As shown, the output pressure is substantially constant but contains a maximum dip at $T_1$, $T_2$, $T_3$, etc., related to the compliance of the system, and the compressibility of the various parts of the system as the pump stroke passes through sufficiently elevated pressure so as to cause flow through the output check valves 40, 42. The maximum of this dip occurs at a time $T_n$ which is variable in delay and directly relatable to the above factors and the actual opening of the valve. The time delay $T_n$ is found to increase in proportion to the operating pressure. In the present invention, this output check valve time delay $T_n$ is measured by the output reading of the output pressure transducer and used as an estimated measure of the time lag $t_n$ (unknown) at which the inlet valve operates. This is found to result in a very satisfactory estimation of inlet valve opening time lag and therefore of the required compensations in actual fill cycle of the components of the mixture being delivered from the composition control valves can be obtained to correspond to that desired.

In the system shown, the pump may be driven by any suitable means but conveniently is driven by a pump driver 63 responsive to a pressure loop 62 having a predetermined reference input delivered to one side of an operational amplifier 64, the other side of which takes pressure sensed by the pressure transducer and compares the same to demand pressure reference 66. If in the normal operating mode, the pump driver delivers a series of output pulses to a stepping motor 68, which in turn drives the cam through its cycle. In this embodiment, the cam is provided with a suitable light interrupters 54 for operating a small LED 56 which provides a start input pulses representing the true beginning of the motion of the piston in the fill portion of each stroke and sends same to a counter 70. The counter counts pulses delivered to a stepping motor and stops when the aforementioned maximum dip in pressure occurs as sensed by the pressure dip sensing circuit 72. This count is a direct measure of the time lag and by adjustment of its value by multiplication of a suitable constant in a time to degree converter 74 results in an output which subtracts this time delay from the demand, thereby giving an output which represents a given recomputed percentage of actual fill cycle which of A obtained. The output of the subtractor 76 drives the composition recomputer 61 and the following valve driver 20 to adjust the remaining solvent component values so that the resultant take-up composition becomes that demanded.

For example, if the delay were found to represent a reduction of the amount of component A desired by 94% at the output of 76, the demand times of B and C would be recomputed by module 61 to be 94% of that originally provided from the isocratic or gradient programmer to result in a composition of carrier containing the originally demanded ratios.

While there has been shown and described a preferred embodiment for carrying out the invention for use with a single pump, three carrier component system, it will be obvious to those skilled in the art that the invention is generally applicable to a system having two or more carrier components. Many other adaptations and applications of the present invention will also occur to those skilled in the art to which it pertains. For example, since the reason that the flow rate of a reciprocating pump falls off with pressure is due to a smaller intake volume at high pressure because of decompression effects, it also follows that a measurement of the time of the maximum pressure dip can also be used to correct flow rate and obtain much better flow accuracy. Accordingly, the scope of the present invention should not be limited by the specific embodiment disclosed, but only by the accompanying claims.

What is claimed is:

1. In liquid chromatographic systems, a method for controlling carrier component proportions delivered from a multi-selecting proportioning valve from a plurality of solvent components A, B . . . sequentially delivered to a pump through an inlet valve, said pump having a fill stroke and an output stroke and capable of causing the composition taken in during the fill stroke to be elevated in pressure and delivered through an outlet valve to an LC column for flow therethrough, the steps of providing a signal indicative of the time of the beginning of the pump fill stroke, providing a signal indicative of the time of pressure dip at the outlet of the pump at the head of the column during the beginning of the pump stroke, computing the time lag between the two signals, computing a proportioning factor based on said time lag to derive a correction factor signal representing the percentage of lost time during the pump fill stroke, applying said correction factor signal to recompute the valve timing required to achieve demand composition based on the correction, and controlling the valve timing of the proportioning valve by said recomputed valve timing.

2. In a liquid chromatograph including an LC column (LC) apparatus, means for combining a plurality of solvents in predetermined composition proportions comprising, a proportioning valve having a time control for selecting each of the solvents in accordance with a predetermined program, a pump, said pump having a fill stroke and an output stroke, inlet valve means for connecting the inlet of said pump connected to the output of said proportioning valve to receive proportions of said solvent components during said fill stroke, said pump being capable when filled of elevating the contents of the fill to a predetermined pressure, check valve means for connecting the outlet of said pump to said LC column, means for measuring the pump output pressure thereat, means responsive to the start of a fill cycle of said pump and responsive to pressure dips as sensed by said pressure transducer for measuring a time lag between the beginning of the time of stroke maximum pressure dip before opening of the output valve in the pressure stroke as sensed by said pressure transducer to thereby derive an empirical measure of the compliance of the system and compressibility of contained carrier at a given operating pressure, means deriving a correction factor for a predetermined operating pressure of said system proportional to the percentage of input of the first solvent component actually taken in by said pump during the beginning of said fill cycle, means for recomputing the timing of the operation of said proportioning valve and for controlling the same to adjust the remaining time intervals so as to adjust the remaining times to compensate for the inlet valve of time lag opening and thereby obtain corrected amounts of solvent components adjusted to the deficiency estimated in the initial component drawn.

3. Apparatus as in claim 2 in which said pump is operated by a stepping motor and in which said measuring means comprises a counter responsive to pulses delivered to said stepping motor,
 means associated with said cam for indicating the start of each fill cycle and for supplying a start signal for said counter,
 means associated with said pressure transducer for measuring a time of maximum dip in system output pressure at the inlet of said column and for delivering said time of lag to said counter as a stop signal to develop a counter output proportional thereto,
 means for said time of lag into an estimate of the percentage of actual fill cycle during which said first component was taken up,
 a composition recomputer responsive to said last named means for developing a corrected value of fill cycle times for the remaining components in proportion to said percentage.

* * * * *